(12) United States Patent
Novotny et al.

(10) Patent No.: US 9,228,265 B2
(45) Date of Patent: Jan. 5, 2016

(54) METALLIC NANO-TIP APPARATUS, METHODS, AND APPLICATIONS

(71) Applicants: UNIVERSITY OF ROCHESTER, Rochester, NY (US); Regents of the University of Minnesota, Minneapolis, MN (US)

(72) Inventors: Lukas Novotny, Pittsford, NY (US); Sang-Hyun Oh, Plymouth, MN (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 14/410,609

(22) PCT Filed: May 10, 2013

(86) PCT No.: PCT/US2013/040469
§ 371 (c)(1),
(2) Date: Dec. 23, 2014

(87) PCT Pub. No.: WO2014/003901
PCT Pub. Date: Jan. 3, 2014

(65) Prior Publication Data
US 2015/0191003 A1    Jul. 9, 2015

Related U.S. Application Data

(60) Provisional application No. 61/666,301, filed on Jun. 29, 2012.

(51) Int. Cl.
| | | |
|---|---|---|
| H01B 13/00 | (2006.01) |
| C23F 1/04 | (2006.01) |
| H01L 21/02 | (2006.01) |
| B81C 1/00 | (2006.01) |
| B82Y 20/00 | (2011.01) |
| B82Y 35/00 | (2011.01) |
| G01Q 60/22 | (2010.01) |
| B32B 43/00 | (2006.01) |
| G01N 21/01 | (2006.01) |
| G01N 21/65 | (2006.01) |

(52) U.S. Cl.
CPC ............ *C23F 1/04* (2013.01); *B32B 43/006* (2013.01); *B81C 1/00111* (2013.01); *B82Y 20/00* (2013.01); *B82Y 35/00* (2013.01); *G01Q 60/22* (2013.01); *H01L 21/0259* (2013.01);
(Continued)

(58) Field of Classification Search
CPC ............. H01L 21/0259; H01L 21/02603; H01L 21/02606; B82Y 10/00; B82Y 15/00; G01Q 70/12
USPC ............................................ 216/17, 18, 39, 40
See application file for complete search history.

(56) References Cited

U.S. PATENT DOCUMENTS 6,417,606 B1 * 7/2002 Nakamoto et al. ............ 313/336
2005/0130551 A1   6/2005 Cross et al.
(Continued)

OTHER PUBLICATIONS

Shi, et al., Aug. 1, 2003,"Ultrahigh Light Transmision Through A C-Shaped Nanoaperture", Optics Letters, vol. 28, No. 15, pp. 1320-1322.
(Continued)

*Primary Examiner* — Binh X Tran
(74) *Attorney, Agent, or Firm* — William Greener; Bond, Schoeneck & King, PLLC

(57) ABSTRACT

Methods for template-stripping a single metallic nano-tip structure from a template containing a plurality of ready-to-be-template-stripped inverted metallic nano-tip structures include attaching the metallic nano-tip structure to a wire handle or a cantilever. A metallic nano-tip assembly includes a single metallic nano-tip structure attached to a handle or mounted on a cantilever structure. The metallic nano-tip assembly may be conductive.

20 Claims, 10 Drawing Sheets

(52) U.S. Cl.
CPC ...... *H01L 21/02603* (2013.01); *B32B 2311/02* (2013.01); *G01N 21/01* (2013.01); *G01N 21/658* (2013.01)

(56) References Cited

U.S. PATENT DOCUMENTS

| | | |
|---|---|---|
| 2006/0018239 A1 | 1/2006 | Nam et al. |
| 2008/0145603 A1 | 6/2008 | Pirovano |
| 2011/0039100 A1 | 2/2011 | Berenschot et al. |
| 2011/0180886 A1* | 7/2011 | El Rifai et al. ............... 257/415 |
| 2011/0270221 A1* | 11/2011 | Ross ............................ 604/506 |
| 2012/0128882 A1* | 5/2012 | Mirkin et al. ............... 427/256 |
| 2012/0260374 A1* | 10/2012 | McConney ..................... 850/1 |
| 2013/0302464 A1* | 11/2013 | Zheng et al. ................. 425/385 |

OTHER PUBLICATIONS

International Search Report Form PCT/ISA2/220, International Application No. PCT/US2013/040469, Dated Aug. 21, 2013, p. 1-12.

* cited by examiner

| | Silicon |
| | Gold |
| | Silicon or Si$_3$N$_4$ |
| | Epoxy | a) Start with isolated pyramid made as before b) Use pre-made tip or tip-less cantilever with a drop of epoxy and align to pyramid c) After epoxy dries, remove the tip from the mold (a)

(b)

- Silicon
- Gold
- Silicon or $Si_3N_4$
- Metal a) Etch pits with potassium hydroxide (KOH) and silicon nitride (Si3N4) mask and deposit Au as before. Remove top metal with tape b) Deposit thick metal to fill mold c) Define cantilever with photolithography from top

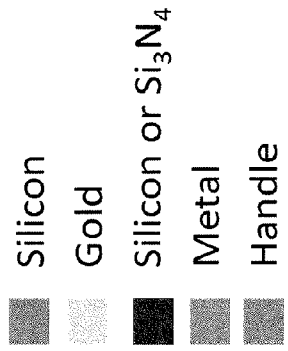
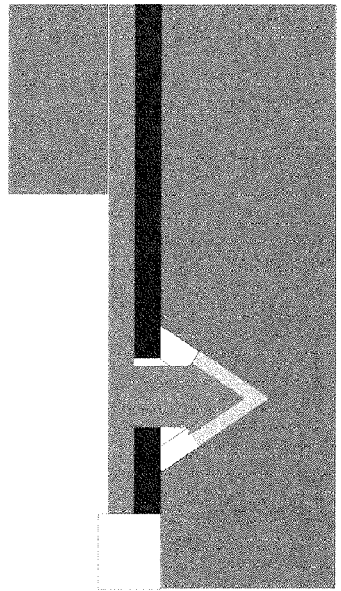
d) Attach to handle (Si, SU-8, glass)
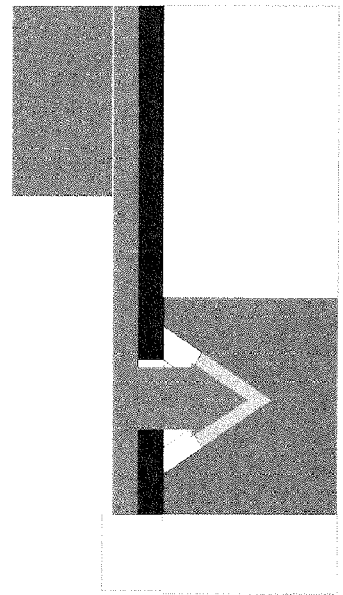
e) Etch away majority (or all) of Si from backside
FIG. 5 (con't)

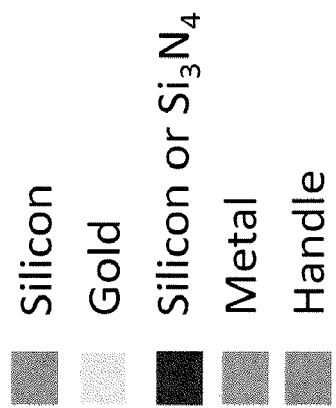
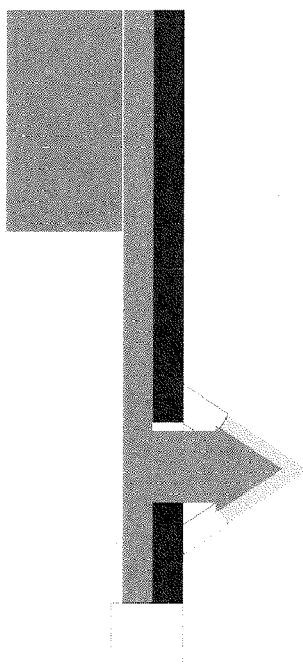
f) Pull away cantilever (Template stripping)
FIG. 5 (con't)

- Silicon
- Gold
- Cantilever material a) Etch pits with KOH, remove silicon nitride mask, and deposit Au everywhere b) Deposit nitride over wafer (PECVD, LPCVD, other). Or deposit other cantilever material (SU-8, Si, $Al_2O_3$)

c) Pattern cantilever

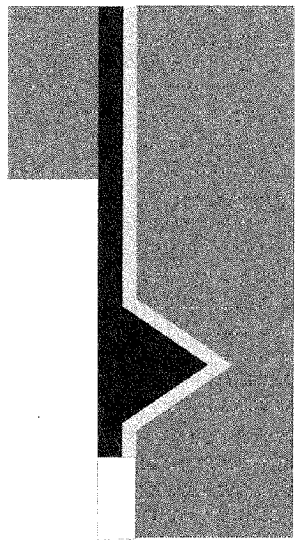
d) Attach to handle (Si, SU-8, glass)
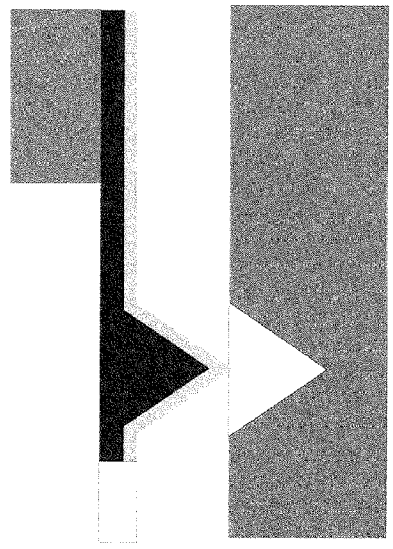
e) Pull cantilever from mold
FIG. 6 (con't)

(a)

(b)

METALLIC NANO-TIP APPARATUS, METHODS, AND APPLICATIONS

This application is a U.S. national phase filing of PCT/US2013/040469, filed May 10, 2013 and claims the benefit thereof, which claims priority to U.S. Provisional Application No. 61/666,301 filed Jun. 29, 2012, the subject matter of which is fully incorporated herein by reference in its entirety.

Embodiments of the invention are most generally directed to metallic nano-tips and more particularly, to methods for template-stripping a single metallic nano-tip from a patterned template, mounted metallic nano-tip assemblies, and applications thereof.

Information about the fabrication of ready-to-be-template-stripped inverted metallic nano-tip structures and more particularly, the mass fabrication of high-quality, uniform, ultra-sharp (<10 nm) metallic probes suitable for single-molecule fluorescence, single molecule tip-enhanced Raman spectroscopy (TERS), and other techniques benefitting from large local field enhancement and high lateral imaging resolution, as disclosed herein can be found at T. W. Johnson et al., "Templated mass production of ultra-sharp metallic probes for near-field optical microscopy," ACS Nano 6, 9168-9174 (2012); Lindquist et al., "Three-Dimensional Plasmonic Nanofocusing," *Nano Lett.* 2010, 10. 1369-1373; Shi et al., "Ultrahigh light transmission through a C-shaped nanoaperture," OPTICS LETTERS/Vol. 28, No. 15/Aug. 1, 2003; http://www.photonics.ethz.ch/en/general-information/research/near-field-optics.html; and International Patent Publication WO/2010/065071, the subject matters of which are fully incorporated herein by reference in their entireties to the fullest extent allowed by applicable laws and rules. As such, it will be understood that the provision of a template containing a plurality of ready-to-be-template-stripped inverted metallic nano-tip structures each having an open base region, wherein said open base region has a dimension, d, in the range from one to 500 micrometers (μm) and/or a silicon (Si) template having a plurality of inverted pyramidal pits defined in a top surface thereof, each inverted pyramidal pit having an open base region, wherein said open base region has a dimension, d, in the range from one to 1000 μm, is known.

FIGS. 1a, 1b, and 1d are scanning electron microscopy (SEM) images of metallic (pyramid-shaped) tips; (a) ~1.5 million nominally identical tips fabricated over an entire wafer (50 μm between pyramids); (b) close up image of a single 200-nm thick gold pyramidal tip resting in an inverted silicon mold; (d) the pyramidal tip having a tip radius of 10 nm, suitable for high-resolution near-field imaging.

Following the mass production of the metallic nano-tips as illustrated in FIG. 1a, utilization of the nano-tips requires removal of single nano-tips from the template (mold). This is the problem confronted in the instant application and the solution provided by the embodied invention. The inventors have recognized the benefits and advantages of simple and reliable methods for template stripping a single metallic nano-tip structure from a template, as well as the beneficial value of providing a metallic nano-tip assembly comprising a metallic nano-tip mounted on a handle, ready for being implemented in, e.g., a near-field scanning optical microscope (NOSM) as illustrated, for example, in FIG. 2.

The use and widespread implementation of NSOM is severely limited by the low reproducibility of near-field probes. Prior to the aforementioned capability to mass fabricate high-quality, uniform, ultra-sharp (<10 nm) metallic probes, there has been no reliable fabrication method that would provide reproducible probes with high yield and throughput. The grain structure and roughness of evaporated metals introduces a high degree of variability in the fabrication of both aperture and tip based near-field probes. Sculpting and shaving of probes by focused ion beam (FIB) milling provides smoother surfaces, but it is slow and costly and leads to unwanted ion implantation. Better reproducibility is achieved with near-field probes made of colloidal metal nanoparticles, but the picking and attaching of single nanoparticles to the end of pulled fibers is painstaking and inefficient. Furthermore, because of quenching, these nanoparticle probes require particles larger than 60 nm, which limits the attainable optical resolution.

An embodiment of the invention is a method for template-stripping a single metallic nano-tip structure from a template. The method includes the steps of providing a template containing a plurality of ready-to-be-template-stripped inverted metallic nano-tip structures each having an open base region, wherein said open base region has a dimension, d, in the range from one to 500 micrometers (μm); providing an elongate handle having a distal end; applying a droplet of adhesive onto or adjacent the distal end of the handle; contacting the droplet of adhesive with the open base region of the inverted metallic nano-tip structure; allowing the adhesive to cure; and removing the single metallic nano-tip structure from the template. According to various non-limiting, exemplary and illustrative aspects, the embodied invention may further, or alternatively be characterized as follows:

wherein d is in the range from one to 300 micrometers (μm);
providing a template containing a plurality of inverted plasmonic nano-tip structures;
wherein the handle is a metallic wire;
   wherein the metallic wire is gold, aluminum, copper, or tungsten;
   wherein the metallic wire has a diameter between about 10-500 μm;
wherein the handle is an optical fiber or a bundle of carbon nanotubes;
   wherein the fiber is coated with a conductive material;
wherein the plurality of inverted metallic nano-tip structures each have an apertured tip, further wherein the handle is a pipette having a capillary;
wherein the handle comprises one of crystalline silicon, polycrystalline silicon, amorphous silicon, $Si_3N_4$, SU-8, polyimide, epoxy, silica, and $Al_2O_3$;
sharpening the distal end of the handle;
wherein applying a droplet of adhesive on the handle further comprises dipping the distal end of the handle into a supply of the adhesive;
applying a droplet of conductive adhesive;
attaching the handle at or adjacent a proximal end of the handle to a cantilever;
   wherein the cantilever is a prong of a quartz tuning fork;
wherein each single nano-tip structure has a pyramidal shape including a tip having a radius of curvature equal to or less than 10 nm;
wherein each single nano-tip structure has a pyramidal shape including a tip having an aperture in the tip.
   wherein the aperture is a C-shaped aperture.

A related embodiment of the invention is a method for template-stripping a single metallic nano-tip structure from a template. The method includes the steps of providing a template containing a plurality of ready-to-be-template-stripped inverted metallic nano-tip structures including a top surface cantilever material, each nano-tip structure having an open base region, wherein said open base region has a dimension, d, in the range from one to 500 micrometers (μm); depositing a layer of a second metal having a thickness between about two –500 μm over the top surface cantilever material including the open base regions of the nano-tip structures such that the layer thickness is sufficient to fill the open base region to connect the metal in the open base region to the metal on the top surface cantilever material; defining a cantilever structure in the cantilever material and the second metal layer; attaching a cantilever handle to a region of the second metal layer; etching away a portion of the template adjacent the inverted metallic nano-tip structures; and removing the inverted metallic nano-tip structure including the cantilever and the cantilever handle from the template. According to various non-limiting, exemplary and illustrative aspects, the embodied invention may further, or alternatively be characterized as follows:

wherein the second metal is tungsten, aluminum, or copper;
photolithographically defining the cantilever structure in the cantilever material and the second metal layer;
wherein the cantilever handle is SU-8;
wherein the cantilever handle is photolithographically defined;
wherein the cantilever handle is silicon (Si) or glass;
wherein the cantilever handle is bonded to the top surface cantilever material;

A related embodiment of the invention is a method for template-stripping a single metallic nano-tip structure from a template. The method includes the steps of providing a Si template having a plurality of inverted pyramidal pits defined in a top surface thereof, each inverted pyramidal pit having an open base region, wherein said open base region has a dimension, d, in the range from one to 1000 micrometers (μm); depositing a layer of metal over the top surface of the template including the plurality of open base regions; depositing a layer of cantilever material over the layer of metal; patterning a cantilever structure including removing the metal layer that is not under the layer of cantilever material; attaching a cantilever handle to a region of the layer of cantilever material; and removing the inverted metallic nano-tip structure including the cantilever structure and the cantilever handle from the template. According to various non-limiting, exemplary and illustrative aspects, the embodied invention may further, or alternatively be characterized as follows:

depositing the layer of metal over the top surface of the template including the plurality of open base regions having a thickness between about 100-1000 nm;
depositing a layer of gold or silver over the top surface of the template including the plurality of open base regions having a thickness between about 100-1000 nm;
depositing a layer of Si, SU-8, $Al_2O_3$, or $Si_3N_4$ cantilever material over the layer of metal;
photolithographically patterning the cantilever structure;
wherein the cantilever handle is SU-8;
wherein the cantilever handle is photolithographically defined.
wherein the cantilever handle is Si or glass;
wherein the cantilever handle is bonded to the region of the cantilever material.

An embodiment of the invention is a metallic nano-tip assembly. The assembly includes a metallic nano-tip; an attachment interface; and an elongate handle having a distal end, wherein the metallic nano-tip is disposed on, or adjacent, the distal end of the elongate handle. According to various non-limiting, exemplary and illustrative aspects, the embodied invention may further, or alternatively be characterized as follows:

wherein the attachment interface is a conductive adhesive;
wherein the handle is a metallic wire;
wherein the metallic wire is gold, aluminum, copper, or tungsten;
wherein the metallic wire has a diameter of between about 10-500 μm;
wherein the handle is an optical fiber or a bundle of carbon nanotubes;
wherein the optical fiber is coated with a conductive material;
wherein the handle is a pipette having a capillary;
wherein the handle is silicon, $Si_3N_4$, SU-8, or $Al_2O_3$;
wherein the distal end of the handle is sharpened;
wherein the attachment interface is an optical adhesive;
wherein the attachment interface is a conductive adhesive;
further comprising a cantilever structure, wherein the handle is fixedly disposed on the cantilever structure at, or adjacent, a proximal end of the handle;
wherein the cantilever structure is a prong of a tuning fork;
wherein each single metallic nano-tip has a pyramidal shape including a tip having a radius of curvature equal to or less than 10 nm;
wherein each single metallic nano-tip structure has a pyramidal shape including a tip having an aperture in the tip;
wherein the aperture is a C-shaped aperture.

The embodied invention will be better understood from the following detailed description and in consideration with the accompanying figures. It is to be expressly understood, however, that each of the figures is provided to further illustrate and describe the invention and are not intended to further limit the invention claimed.

FIG. 1 shows scanning electron microscopy (SEM) images of ready-to-be-template-stripped or template-stripped metallic tips; (a) a template (Si wafer) having ~1.5 million nominally identical metallic nano-tips can be fabricated over an entire wafer, as known in the art; (b) close up image of a single 200-nm thick gold nano-tip resting in the inverted silicon mold after lift-off, as known in the art; (c) SEM image after template striping with epoxy and a thin tungsten wire, according to an illustrative embodiment of the invention; (d) the metallic pyramidal tip having a tip radius of 10 nm, suitable for high-resolution near-field imaging, as known in the art.

FIG. 2 schematically illustrates a setup used for near-field imaging with template-stripped gold pyramidal tips, according to an illustrative aspect of the invention.

FIGS. 3(a, b, c) schematically illustrate a method for template-stripping a single metallic nano-tip structure from a template, according to an illustrative embodiment of the invention.

FIGS. 4(a, b) show SEM images of a metallic pyramidal nano-tip mounted on the end of a wire handle, according to illustrative embodiments of the invention; a) a 20 micron gold pyramid on a 15 micron tungsten wire; b) a 55 micron gold pyramid on a 50 micron tungsten wire.

FIGS. 5(a-f) schematically illustrate a method for template-stripping a single metallic nano-tip structure from a template, according to an illustrative embodiment of the invention.

FIGS. 6(a-e) schematically illustrate a method for template-stripping a single metallic nano-tip structure from a template, according to an illustrative embodiment of the invention.

FIGS. 7(a, b) show different views of a metallic pyramidal nano-tip mounted on a cantilever, according to an illustrative embodiment of the invention.

A method for template-stripping a single metallic nano-tip structure from a template is illustrated with reference to FIGS. 3(a, b, c). The process is more completely described as template-stripping a single metallic nano-tip structure from a template (Si wafer) (FIG. 3a) containing a plurality of ready-to-be-template-stripped inverted metallic nano-tip structures (FIG. 1a) each having an open base region of from about one to about 1000 micrometers (μm) (this value depending upon the dimensions of the Si wafer/template). For a standard four (4) inch diameter Si wafer having a thickness of about 500 μm, the open base region of the inverted pyramidal nano-tip structure will likely be from about one to about 500 μm or even from about one to about 300 μm. As illustrated in FIG. 3b, an elongate handle structure is provided. The handle structure may be a metallic wire, e.g., made of gold, aluminum, copper, or tungsten, having a diameter between about 10-500 μm. Alternatively, the handle may be an optical fiber or a bundle of carbon nanotubes. If the mounted nano-tip assembly is to be conductive, a fiber handle may be coated with a conductive material. The handle may also be made from crystalline silicon, polycrystalline silicon, amorphous silicon, $Si_3N_4$, SU-8, polyimide, epoxy, silica, or $Al_2O_3$. In an exemplary aspect, the cantilever is a prong of a quartz tuning fork. The distal (connection) end of the handle may be pointed, tapered, or otherwise sharpened.

A suitable amount (e.g., a droplet) of adhesive is then applied on the distal end of the handle or adjacent (near) the distal end of the handle as illustrated in FIG. 3b. An exemplary adhesive is conductive epoxy such as NCA 130 (Norland, #13001) and UHU Schnellfest two-part epoxy (Restorer Supplies Inc.). A drop of adhesive may be applied directly to the distal end of the handle or, alternatively, the distal end of the handle may be dipped into a quantity of the adhesive.

The end of the handle with the adhesive is then aligned over the open base region of the pyramidal nano-tip and brought ever closer to the open tip region until there is contact of the adhesive droplet with the open base region of the inverted metallic nano-tip structure. The bond is allowed to form and the single metallic nano-tip structure can be removed from the template as illustrated in FIG. 3c.

In the case where the metallic nano-tip has an aperture (e.g., C-shaped aperture) in the tip, as known in the art, the handle may be a pipette having a capillary to transmit light there through.

Figure 5:
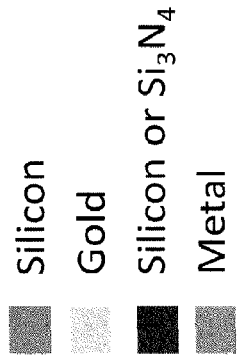
Figure 5:
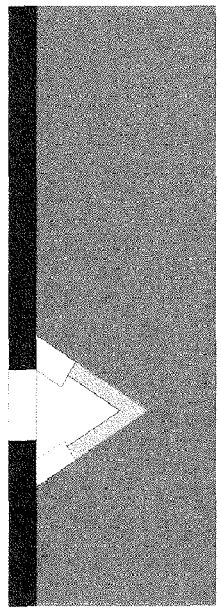
Figure 5:
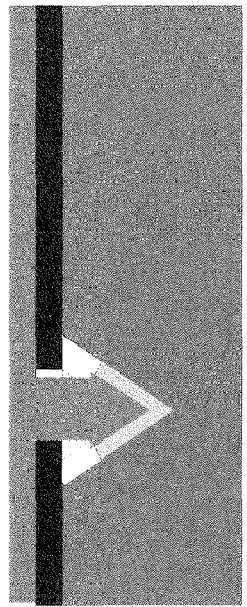
Figure 5:
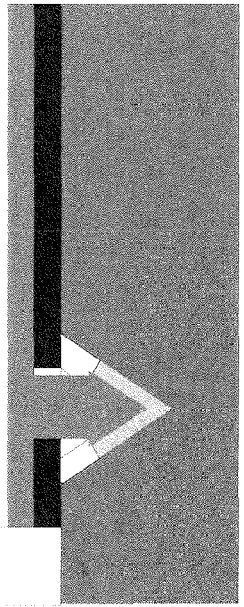

FIGS. 5(a-f) schematically illustrate a related method for template-stripping a single metallic nano-tip structure from a template. As before, a template containing a plurality of ready-to-be-template-stripped inverted metallic nano-tip structures is provided. In an exemplary aspect as illustrated in FIG. 5a, circular apertures between about one to 500 μm in diameter are patterned in the cantilever material, e.g., Si or $Si_3N_4$. The Si template is then etched in KOH to create the pyramidal pits. Between about 100 nm-1000 nm Au is then deposited on the wafer and the Au which is not in the pyramidal pits is removed from the top surface with tape or another polymer.

As illustrated in FIG. 5b, a second layer of metal (e.g., W, Al, or Cu) with a thickness between about two to 500 μm is deposited on the wafer. The material should be thick enough to fill the pyramidal pit to connect the metal in the pit to the metal on the top surface.

As illustrated in FIG. 5c, photolithography is used to define the cantilever in both the cantilever material and the deposited metal layer.

As illustrated in FIG. 5d, the cantilever is then attached to a handle. The handle may be SU-8 and defined with photolithography, or could be Si or glass and bonded to the cantilever.

As illustrated in FIG. 5e, the Si substrate is then etched away leaving only the portion containing the pyramidal pit.

As illustrated in FIG. 5f, the cantilever is then template-stripped from the mold.

Figure 6:
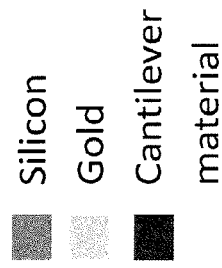
Figure 6:
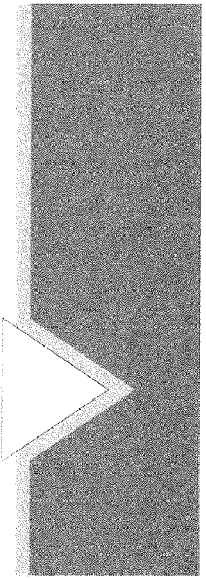
Figure 6:
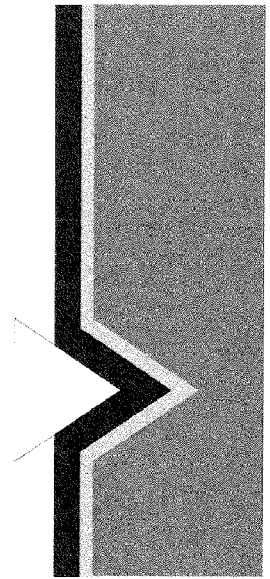
Figure 6:
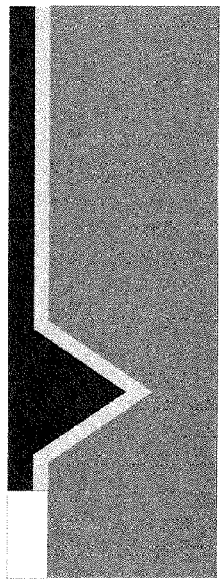
Figure 7:
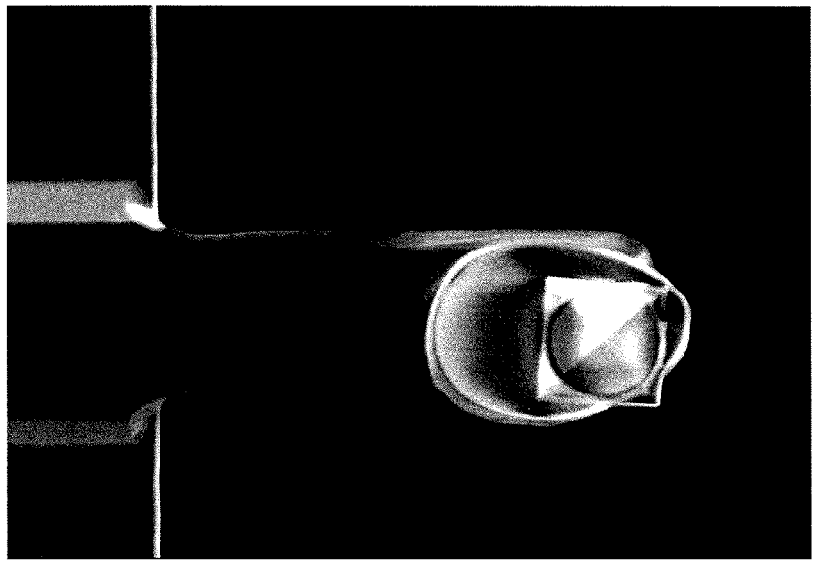
FIGS. 7(a, b) show different views of a metallic (Au) pyramidal nano-tip mounted on a cantilever, according to the exemplary embodiments of the invention.
Figure 7:
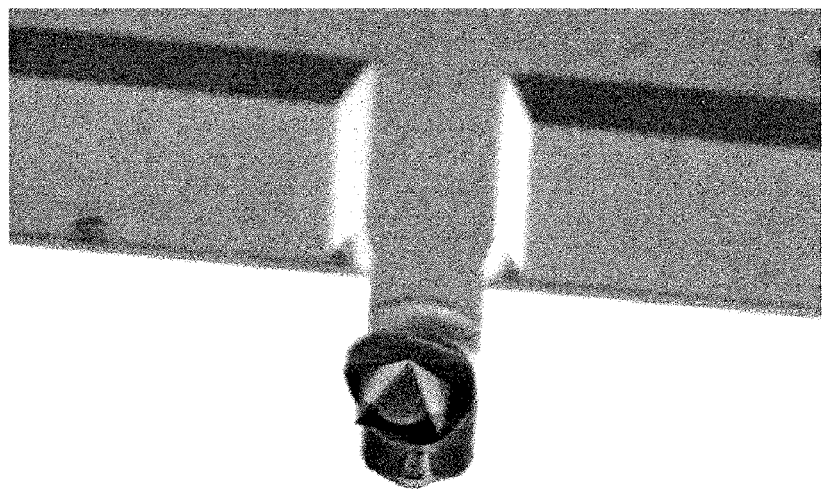

FIGS. 6(a-e) schematically illustrate a related method for template-stripping a single metallic nano-tip structure from a template. As before, a template containing a plurality of ready-to-be-template-stripped inverted metallic nano-tip structures is provided. In an exemplary aspect as illustrated in FIG. 6a, a layer of gold or silver (Ag) between about 100-1000 nm is deposited on the Si template surface including the etched open bases of the pyramidal pits.

As illustrated in FIG. 6b, a layer of cantilever material (e.g., nitride deposited by PECVD, LPCVD or another method, or other materials such as SU-8, Si, or $Al_2O_3$) is applied over the Au or Ag layer.

As illustrated in FIG. 6c, the cantilever is photolithographically patterned and the Au (or Ag) that is not under the cantilever is removed.

As illustrated in FIG. 6d, the cantilever is then attached to a handle (which could be any of the handle materials referred to hereinabove).

As illustrated in FIG. 6e, the whole cantilever can then be removed from the mold, since the adhesion between the Si and Au (or Ag) is poor.

Figure 1:
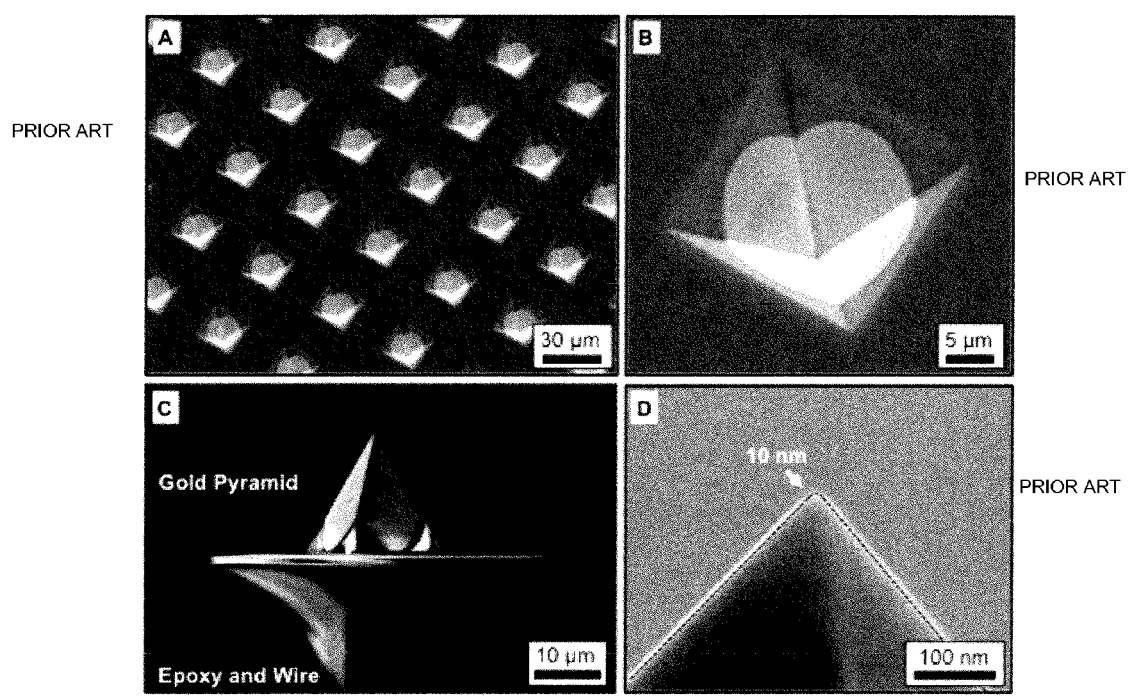
Figure 2:
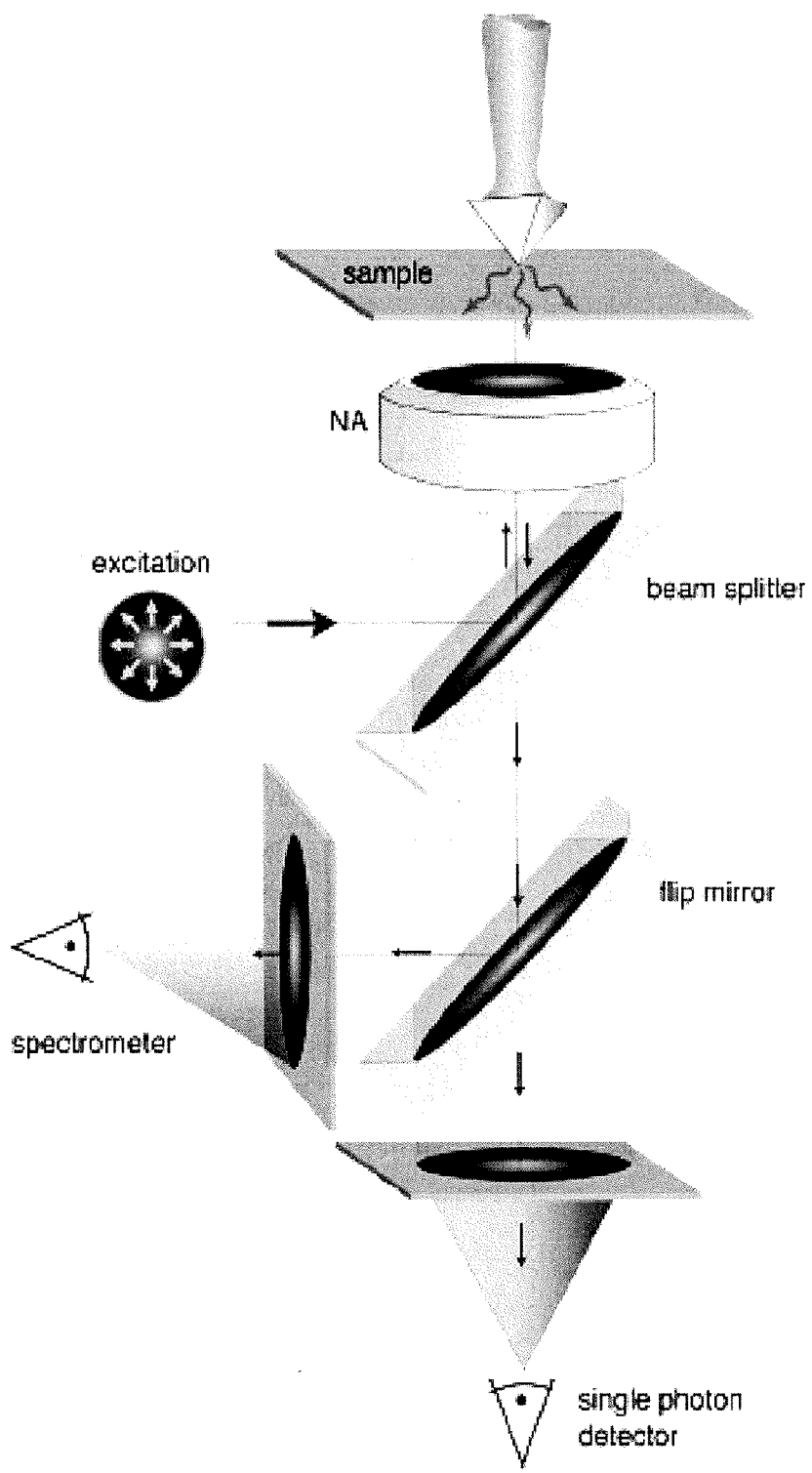
Figure 3:
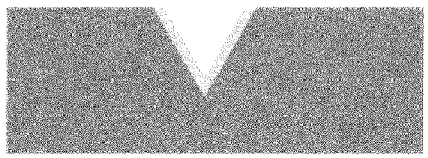
Figure 3:
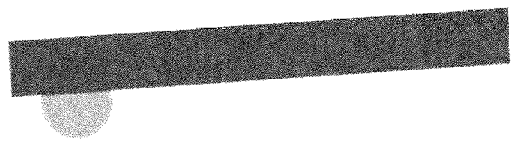
Figure 3:
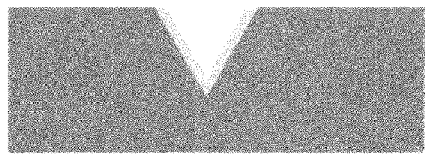
Figure 3:
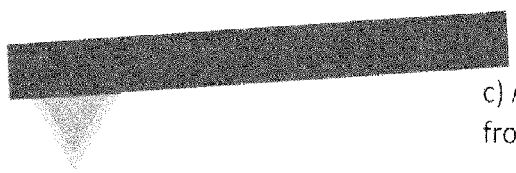
Figure 4:
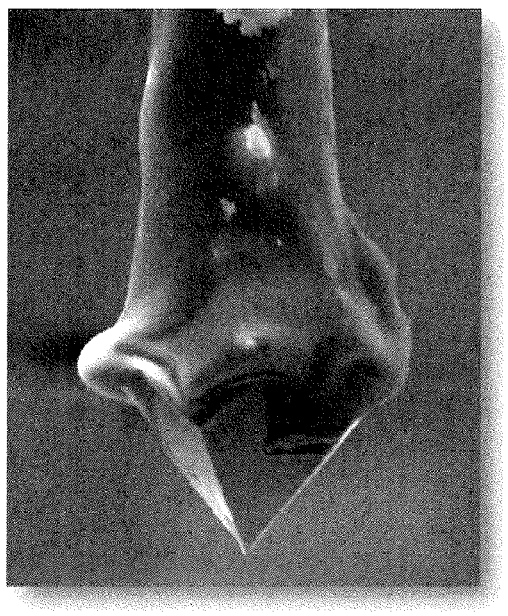
FIGS. 4(a, b) are SEM images showing, respectively, a) a 20 micron gold pyramid picked using a 15 micron tungsten wire; and b) a 55 micron gold pyramid picked using a 50 micron tungsten wire.
Figure 4:
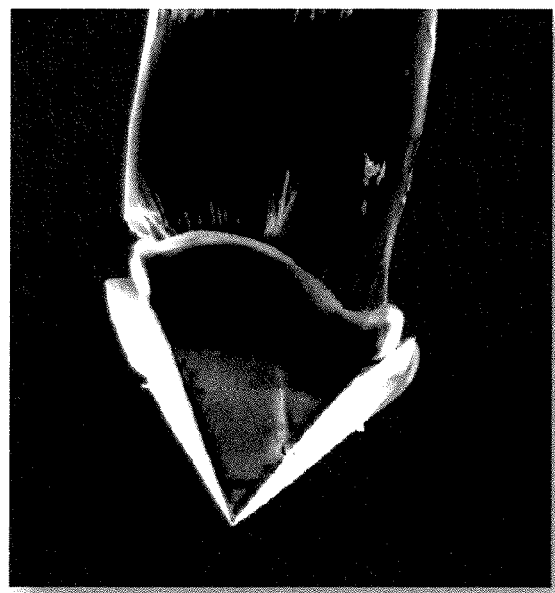

The template-stripped metallic nano-tip disposed on a handle or cantilever, as shown in FIGS. 1c, 4(a, b) and 7(a, b) includes a metallic nano-tip, an attachment interface, and an elongate handle having a distal end, wherein the metallic nano-tip is disposed on, or adjacent, the distal end of the elongate handle. The metallic nano-tip assembly is suitable for single-molecule fluorescence, single molecule tip-enhanced Raman spectroscopy (TERS), and other techniques benefitting from large local field enhancement and high lateral imaging resolution and use in a setup, e.g., as illustrated in FIG. 2 used for near-field imaging with template-stripped gold pyramidal tips. As illustrated in FIG. 2, a radially polarized laser beam is focused on a sample surface. A metallic nano-tip assembly is centered into the diffraction-limited spot generating an enhanced field concentrated at the tip-sample junction and generating a local optical response (e.g., scattering, fluorescence, Raman scattering etc.). The optical response is collected with the same objective lens and directed to a spectrometer or a single-photon counting detector while the sample is raster-scanned.

In various non-limiting aspects of the embodied metallic nano-tip assembly, the attachment interface may be a conductive adhesive. The handle may be a metallic wire of gold, aluminum, copper, or tungsten having a diameter between about 10-500 μm. Alternatively, the handle may be an optical fiber (with or without a conductive coating) or a bundle of carbon nanotubes. The metallic nano-tip may have an aperture in the tip, and the handle may be a pipette having a capillary. The handle may be made from silicon, $Si_3N_4$, SU-8, or $Al_2O_3$.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. The term "about" when prefacing a dimension means the exact value of the recited dimension or substantially the value of the recited dimension within a reasonable accuracy tolerance as understood by a person skilled in the art.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. A method for template-stripping a single metallic nano-tip structure from a template, comprising the steps of:
   providing a template containing a plurality of ready-to-be-template-stripped inverted metallic nano-tip structures each having an open base region, wherein said open base region has a dimension, d, in the range from one to 500 micrometers (μm);
   providing an elongate handle having a distal end;
   applying a droplet of adhesive onto or adjacent the distal end of the elongate handle;
   contacting the droplet of adhesive with the open base region of the inverted metallic nano-tip structure;
   allowing the adhesive to cure; and
   removing the single metallic nano-tip structure from the template.

2. The method of claim 1, wherein d is in the range from one to 300 micrometers (μm).

3. The method of claim 1, comprising providing a template containing a plurality of inverted plasmonic nano-tip structures.

4. The method of claim 1, wherein the plurality of inverted metallic nano-tip structures each have an apertured tip, further wherein the elongate handle is a pipette having a capillary.

5. The method of claim 1, wherein the elongate handle comprises one of crystalline silicon, polycrystalline silicon, amorphous silicon, $Si_3N_4$, SU-8, polyimide, epoxy, silica, and $Al_2O_3$.

6. The method of claim 1, further comprising sharpening the distal end of the elongate handle.

7. The method of claim 1, wherein the elongate handle is an optical fiber or bundles of carbon nanotubes.

8. The method of claim 7, wherein the optical fiber is coated with a conductive material.

9. The method of claim 1, wherein the elongated handle is a metallic wire.

10. The method of claim 9, wherein the metallic wire is one of gold, aluminum, copper, and tungsten.

11. The method of claim 9, wherein the metallic wire has a diameter between about 10 -500 μm.

12. A method for template-stripping a single metallic nano-tip structure from a template, comprising the steps of:
    providing a template containing a plurality of ready-to-be-template-stripped inverted metallic nano-tip structures including a top surface cantilever material, each inverted metallic nano-tip structure having an open base region, wherein said open base region has a dimension, d, in the range from one to 500 micrometers (μm);
    depositing a layer of a second metal having a thickness between about two -500 μm over the top surface cantilever material including the open base regions of the inverted metallic nano-tip structures such that the layer thickness is sufficient to fill the open base region to connect the metal in the open base region to the second metal on the top surface cantilever material;
    defining a cantilever structure in the cantilever material and the second metal layer;
    attaching a cantilever handle to a region of the second metal layer;
    etching away a portion of the template adjacent the inverted metallic nano-tip structures; and
    removing the inverted metallic nano-tip structure including the cantilever, the second metal layer, and the cantilever handle from the template.

13. The method of claim 12, wherein the second metal is one of tungsten, aluminum, and copper.

14. The method of claim 12, further comprising photolithographically defining the cantilever structure in the cantilever material and the second metal layer.

15. A method for template-stripping a single metallic nano-tip structure from a template, comprising the steps of:
    providing a Si template having a plurality of inverted pyramidal pits defined in a top surface thereof, each inverted pyramidal pit having an open base region, wherein said open base region has a dimension, d, in the range from one to 1000 micrometers (μm);
    depositing a layer of metal over the top surface of the template including the plurality of open base regions, thus forming an inverted metallic nano-tip structure;
    depositing a layer of cantilever material over the layer of metal;
    patterning a cantilever structure including removing the metal layer that is not under the layer of cantilever material;
    attaching a cantilever handle to a region of the layer of cantilever material; and removing the inverted metallic nano-tip structure including the cantilever structure and the cantilever handle from the template.

16. The method of claim 15, further comprising depositing a layer of one of Si, SU-8, $Al_2O_3$, and $Si_3N_4$ cantilever material over the layer of metal.

17. The method of claim 15, further comprising photolithographically patterning the cantilever structure.

18. The method of claim 15, wherein the cantilever handle is bonded to the region of the cantilever material.

19. The method of claim 15, further comprising depositing the layer of metal over the top surface of the template including the plurality of open base regions having a thickness between about 100-1000 nm.

20. The method of claim 19, further comprising depositing a layer of gold or silver over the top surface of the template including the plurality of open base regions having a thickness between about 100-1000 nm.

* * * * *